(12) United States Patent
Sieracki et al.

(10) Patent No.: US 7,796,256 B2
(45) Date of Patent: Sep. 14, 2010

(54) OIL-IMMERSION ENHANCED IMAGING FLOW CYTOMETER

(75) Inventors: Christian K. Sieracki, Edgecomb, ME (US); Kent A. Peterson, Yarmouth, ME (US)

(73) Assignee: Fluid Imaging Technologies, Inc., Yarmouth, ME (US)

( * ) Notice: Subject to any disclaimer, the term of this patent is extended or adjusted under 35 U.S.C. 154(b) by 60 days.

(21) Appl. No.: 12/151,262

(22) Filed: May 5, 2008

(65) Prior Publication Data
US 2009/0273774 A1 Nov. 5, 2009

(51) Int. Cl.
*G01N 21/00* (2006.01)
(52) U.S. Cl. .......... 356/342; 356/377; 356/440; 356/72; 250/339.12
(58) Field of Classification Search .......... 356/342, 356/318, 337; 250/458.1; 436/534
See application file for complete search history.

(56) References Cited

U.S. PATENT DOCUMENTS

| 4,612,614 | A | | 9/1986 | Deindoerfer et al. |
| 4,673,288 | A | * | 6/1987 | Thomas et al. ............... 356/72 |
| 4,818,103 | A | * | 4/1989 | Thomas et al. ............... 356/72 |
| 5,159,397 | A | | 10/1992 | Kosaka et al. |
| 5,159,398 | A | | 10/1992 | Maekawa et al. |
| 5,247,339 | A | | 9/1993 | Ogino |
| 5,247,340 | A | | 9/1993 | Ogino |
| 5,248,451 | A | | 9/1993 | Tsunaga et al. |
| 5,471,294 | A | | 11/1995 | Ogino |
| 5,824,269 | A | * | 10/1998 | Kosaka et al. ............... 422/73 |
| 5,852,498 | A | * | 12/1998 | Youvan et al. ............... 356/417 |
| 6,115,119 | A | | 9/2000 | Sieracki et al. |
| 6,525,875 | B1 | * | 2/2003 | Lauer ............... 359/371 |
| 2006/0177937 | A1 | | 8/2006 | Kurabayashi et al. |
| 2006/0197032 | A9 | | 9/2006 | Oostman, Jr. et al. |
| 2007/0184471 | A1 | | 8/2007 | Yguerabide et al. |
| 2009/0125242 | A1 | * | 5/2009 | Choi et al. ............... 702/19 |

OTHER PUBLICATIONS

Notification of International Search Report and Written Opinion in corresponding PCT application No. PCT/US09/02562, dated Jul. 17, 2009, 7 pp.

* cited by examiner

*Primary Examiner*—Tarifur R. Chowdhury
*Assistant Examiner*—Isiaka O Akanbi
(74) *Attorney, Agent, or Firm*—Verrill Dana, LLP; Chris A. Caseiro

(57) ABSTRACT

A flow chamber, imaging objective, condenser and imaging light source as part of an optical system includes an oil-immersion objective and high numerical aperture condenser matched to a rectangular flow chamber. The oil-immersion objective and flow chamber include a high index of refraction immersion oil so as to enhance the optical resolution and optical coupling therethrough. The imaging light source generates light which passes through the condenser, the flow chamber and then the objective before being focused onto an imaging camera. Fluorescence excitation passes through the objective to the flow chamber where the oil immersion configuration enhances the focus and collection of the light back through the objective.

16 Claims, 4 Drawing Sheets

OIL-IMMERSION ENHANCED IMAGING FLOW CYTOMETER

BACKGROUND OF THE INVENTION

1. Field of the Invention

The present invention relates generally to an optical flow imaging and analysis configuration used in particle analysis instrumentation, and more particularly to a high numerical aperture optical flow imaging system incorporating a flow chamber, immersion oil and high numerical aperture optics, including a high numerical aperture oil-immersion objective.

2. Description of the Prior Art

The art has seen various optical/flow systems employed for transporting a fluid within an analytical instrument to an imaging and optical analysis area. A liquid sample is typically delivered into the bore of a flow chamber and this sample is interrogated in some way so as to generate analytical information concerning the nature or properties of the sample. For example, a laser beam may excite the sample that is present in the bore of the capillary, with the emitted fluorescence energy representing the signal information.

From an optical perspective, the objectives and flow chambers in the prior art have been of medium numerical aperture (NA). A typical flow cytometer comprises a cylindrical or rectangular glass rod having a hollow co-axial cylindrical or rectangular bore of smaller diameter, in which the sample to be analyzed is placed. With the sample in place, optical analysis is performed with low to medium numerical aperture (NA) optics (e.g., NA=0.6), typically an air objective. Such low to medium NA optics only are employed in present flow cytometry systems because they are considered easier to use and more suitable for dealing with the limitation of having the fluid of interest spaced from the optics by the thickness of the rod wall, which are simply too thick to permit use of high NA optics.

The inefficiencies of optically imaging with air microscope objectives into and out of the flow cell may include a mediocre resolution, less-than-optimum collection of the image illumination energy from the sample, less than optimum illumination of the sample with fluorescence excitation light and less than optimum collection of fluorescence emissions from the sample.

To date, therefore, the imaging flow cytometer art has not disclosed utilizing oil-immersion objectives to deliberately optimize the imaging resolution and fluorescence excitation and fluorescence emission collection. There is therefore a need in the art for a simple and economical mechanism to increase the resolution and fluorescence efficiency.

SUMMARY OF THE INVENTION

It is an object of the present invention to provide an imaging flow cytometer with improved imaging resolution, fluorescence excitation and fluorescence emission collection. It is also an object of the present invention to provide such an imaging flow cytometer that may be incorporated into, or operate in a similar manner as that of, existing imaging flow cytometers. These and other objects are achieved with the present invention, which enables high resolution through introduction of the combination of an oil-immersion interface and a high NA objective. Such improved resolution capability is suitable for imaging particles associated with, but not limited to, the analysis and/or imaging of nanotechnology particles, bacteria, blood and submicron particles. While it is noted that oil immersion viewing is known in regard to the use of microscope objectives, additional complexities associated with flow cytometry have heretofore rendered the use of oil immersion techniques undesirable or otherwise perceived too difficult to overcome.

The present invention is an optical system including a flow chamber, an imaging objective, and an imaging light source, as well as an oil-immersion objective and a high NA condenser matched to the flow chamber. The oil-immersion objective and the flow chamber include a high index of refraction immersion oil so as to enhance the optical resolution and optical coupling therethrough. The imaging light source generates light which passes through the condenser, the flow chamber and then the objective before being focused onto an imaging camera. Fluorescence excitation passes through the objective to the flow chamber where the oil immersion configuration enhances the focus and collection of the light back through the objective. This combination enables high imaging resolution in the context of an imaging system understandable by those of skill in the art of using such systems. The present system provides sharper, more detailed imaging than available with existing imaging cytometry. Further, the invention enables the ability to produce images of smaller particles in a fluid, and to image smaller details of observed particles. Yet further, the present invention enables the ability to detect smaller and/or weaker fluorescent particles.

This and other advantages of the present invention will become more readily apparent upon review of the following detailed description, the accompanying drawings and the appended claims.

DETAILED DESCRIPTION OF THE PREFERRED EMBODIMENT

Figure 1:
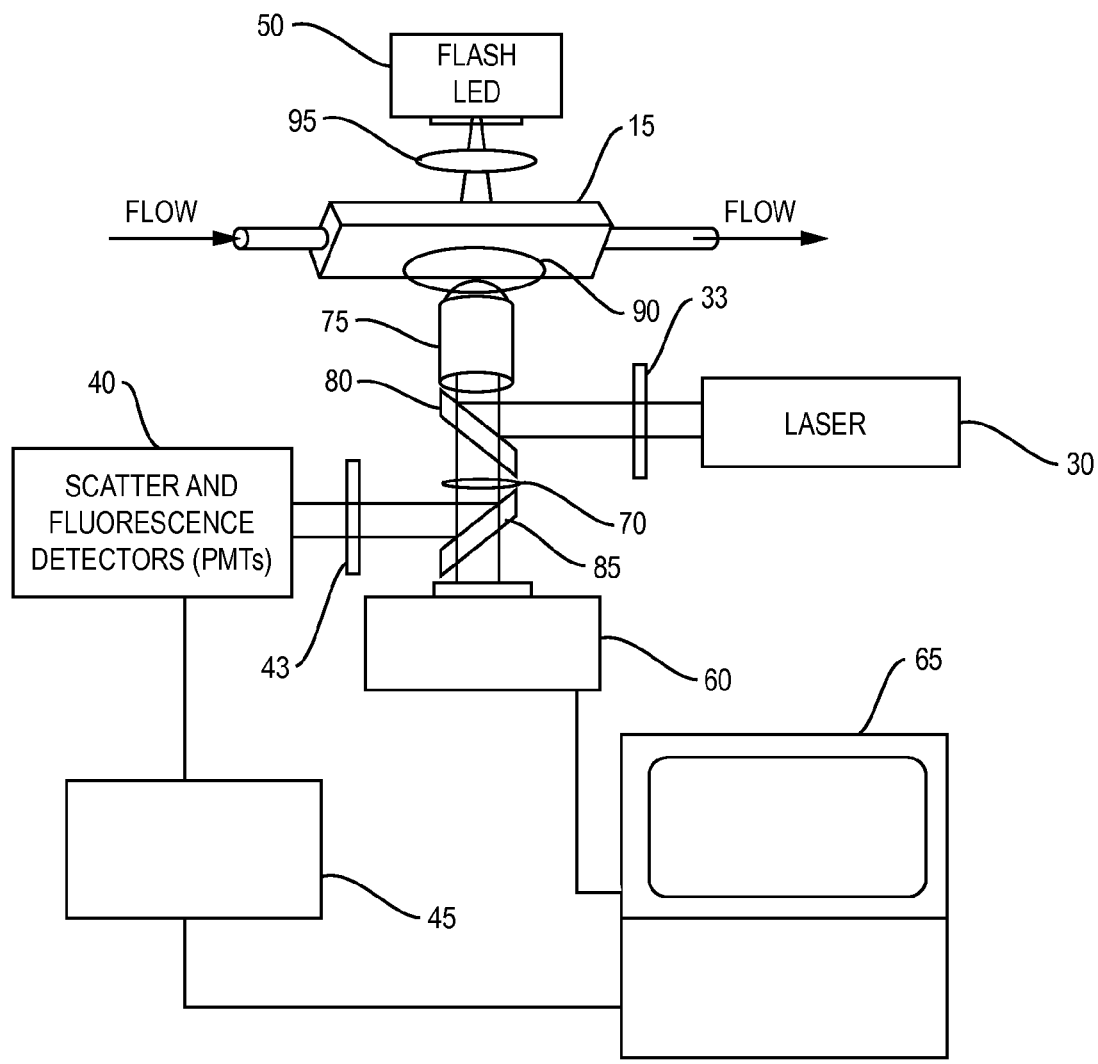
FIG. 1 schematically illustrates a system for studying particles in a fluid according to one embodiment of the invention.
Figure 2:
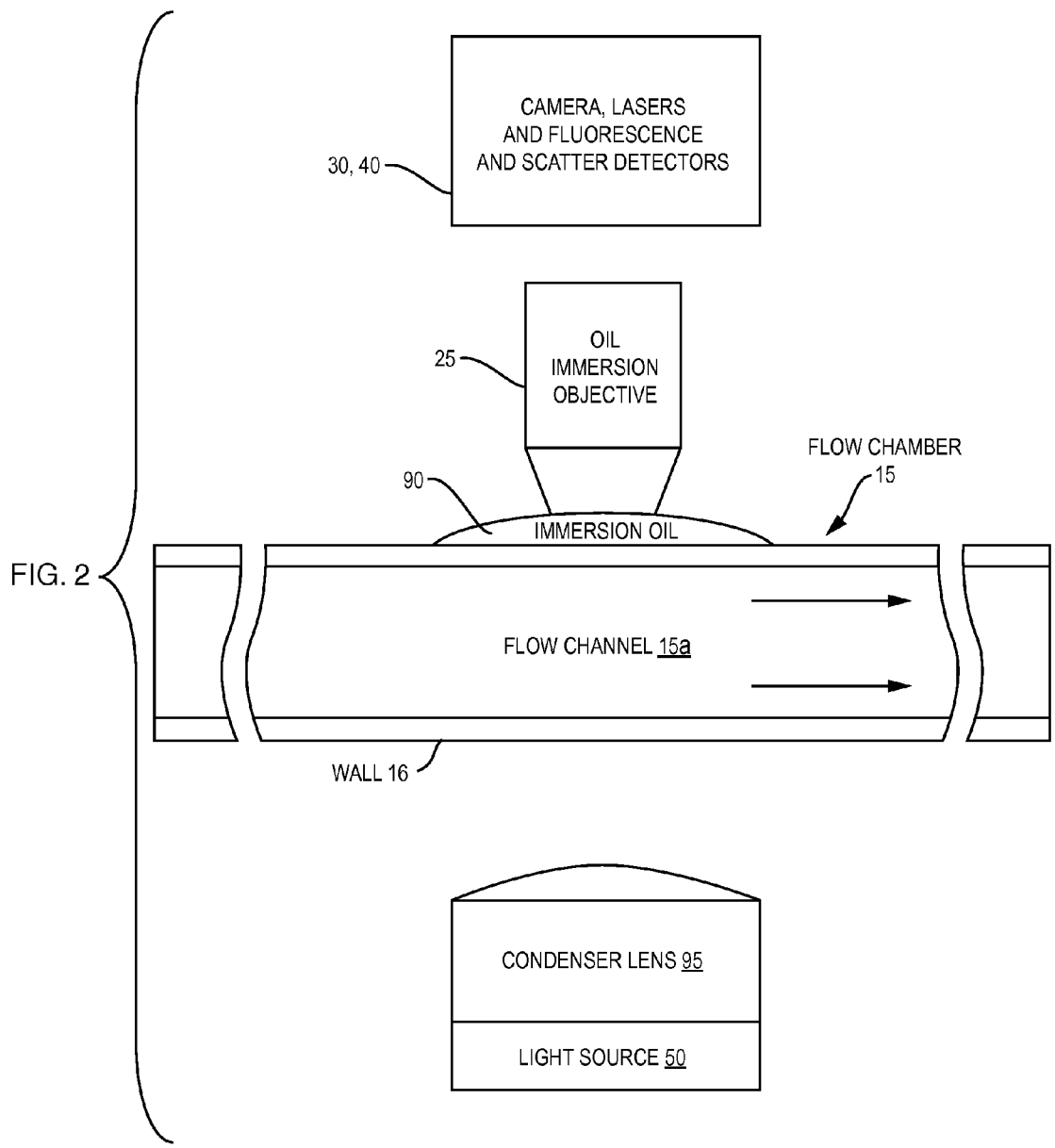
FIG. 2 is an enlarged perspective view of the oil immersion optics and flow chamber of the system of FIG. 1.

A system 10 of the present invention suitable for high quality automated counting and imaging of particles that exist in a fluid is shown in FIGS. 1 and 2. The system 10 includes a flow chamber 15, a light source 30, optics 35, an image detection system 40, a backlighting generator 50, an image capturing system 60, a computing device 65, a high NA objective 75, an immersion oil 90, and a high NA condenser lens 95. The combination of these components of the system 10 arranged and configured as described herein enable a user to detect particles in the fluid and produce high resolution images of those particles in a manner not enabled by existing flow cytometers.

The flow chamber 15 includes an inlet 20 for receiving the particle-containing fluid to be observed, and an outlet 25 through which the fluid passes out of the flow chamber 15 after imaging functions have been performed. The flow chamber 15 is a low fluorescence structure. That is, it may be fabricated of a material that does not readily fluoresce, including, for example, but not limited to, microscope glass or rectangular glass extrusions. The flow chamber 15 may be circular or rectangular in shape. The flow chamber 15 defines a channel 15a through which the fluid flows at a predetermined selectable rate. The channel 15a may be of rectangular configuration. The flow chamber 15 is fabricated with a wall thickness that substantially matches the thickness considered suitable by the manufacturer of the high NA objective 75 described herein. For example, the wall thickness of the flow chamber 15 should substantially match that of a microscope cover slide. The inlet 20 of the flow chamber 15 is connectable to a fluid source and the outlet 25 is connectable to a downstream means for transferring the fluid away from the flow chamber 15.

A light source 30 is used to generate fluorescence and scatter excitation light which is passed through the optics 35 to the flow chamber 15, resulting in particle fluorescence and/or light scatter. The light source 30 may be a laser 30 with an excitation filter 33. The laser 30 may be, but is not limited to being, a 470 nanometer (nm), 488 nm or 532 nm solid state model laser available from an array of manufacturers known to those of skill in the art. The excitation filter 33 should at least have the characteristic of being able to transmit light at wavelengths longer than the wavelengths of light generated by the laser 30. An example of a suitable form of the excitation filter 33 is a 505DCLP longpass filter of the type that can be used with a 488 nm laser available from Chroma Technologies of Rockingham, Vt. US; those of skill in the art will recognize that other suitable filters may be employed for the excitation filter 33. Any particle fluorescence emissions from the flow chamber 15 that have a wavelength of 535 to 900 nm are detected by the detection system 40, which includes at least one or more emission filters 43 and one or more high sensitivity photomultiplier tubes (PMT) 44. The emission filters 43 should at least have the characteristic of being transparent to the fluorescence emissions of a desired fluorophone. An example of a suitable form of an emission filter 43 is a 570/40 phycoerithyn emission filter available from Chroma Technologies of Rockingham, Vt. US; those of skill in the art will recognize that other suitable filters may be employed for the emission filter 43. The PMTs 44 should at least have the characteristic of being sensitive to the fluorescence emissions desired. An example of a suitable form of a PMT 44 is the H9656-20 model available from the Hammamatsu company of Bridgewater, N.J. US; those of skill in the art will recognize that other equivalent PMTs may be employed for the PMT 44. Output from the PMT 44 output is processed by detection electronics 45. Preferably, the detection electronics 45 includes user-adjusted gain and threshold settings which determine the amount of fluorescence or scatter required for the system 10 to acknowledge a passing particle. The detection electronics 45 may be configured to receive input signals and produce output information compatible with the specific needs of the user of the system 10. An example of a suitable electronics system capable of performing the signal activation and output information associated with the detection electronics 45 of the system 10 is the detection electronics described in U.S. Pat. No. 6,115,119 issued Sep. 5, 2000, the entire content of which is incorporated herein by reference. Those of ordinary skill in the art will recognize that the specific electronics system described therein may be modified, such as through suitable programming for example, to trigger desired signal activation and/or to manipulate received signals for desired output information.

If a sufficiently fluorescent particle passes through the flow chamber 15 a fluorescence signal from the PMT 44 is sent to the detection electronics 45, which then generate one or more trigger signals that are transmitted to the computing device 65. The computing device 65 is programmed to store the information received from the detection electronics 45 and to make calculations associated with the particles detected. For example, but not limited thereto, the computing device 65 may be programmed to provide specific information regarding the fluorescence of the detected particles, the shape of the particles, dimensions of the particles, and specific features of the particles. The computing device 65 may be any sort of computing system suitable for receiving information, running software programs on its one or more processors, and producing output of information, including, but not limited to images and data, that may be observed on a user interface.

The detection electronics 45 may also be coupled, directly or indirectly through the computing device 65 to the backlighting generator 50. In particular, the detection electronics 45 and/or the computing device 65 may include an arrangement whereby a user of the system 10 may alternatively select a setting to automatically generate a trigger signal at a selectable time interval. The trigger signal generated produces a signal to activate the operation of the backlighting generator 50 so that a light flash is generated. Specifically, the backlighting generator 50 may be a Light Emitting Diode (LED) or other suitable light generating means that produces a light of sufficient intensity to backlight the flow chamber 15 and image the passing particles. The very high intensity LED flash may be a 670 nm LED flash, or a flash of another other suitable wavelength, which is flashed on one side of the flow chamber 15 for 200 μsec (or less). At the same time, the image capturing system 60 positioned on the opposing side of the flow chamber 15 is activated to capture an instantaneous image of the particles in the fluid as "frozen" when the high intensity flash occurs. The image capturing system 60 is arranged to either retain the captured image, transfer it to the computing device 65, or a combination of the two. The image capturing system 60 includes characteristics of a digital camera or an analog camera with a framegrabber or other means for retaining images. For example, but in no way limiting what this particular component of the system may be, the image capturing system 60 may be, but is not limited to being, a CCD firewire, a CCD USB-based camera, or other suitable device that can be used to capture images and that further preferably includes computing means or that may be coupled to computing means for the purpose of retaining images and to manipulate those images as desired. The computing device 65 may be programmed to measure the size and shape of the particle captured by the image capturing system 60 and/or store the data for later analysis.

An aspect of the improved imaging capability associated with the use of the system 10 of the present invention is the inclusion of the high NA objective 75, the immersion oil 90 and the high NA condenser lens 95 as part of the optics 35. The high NA condenser lens 95 aids in clear illumination of that section of the fluid in the flow channel 15a that is to be imaged by focusing the high intensity flash from the backlighting generator 50 to that section. The high NA condenser lens 95 includes characteristics of a numerical aperture of about 1.25 and may be the AA2354932 1.25NA Abbe condenser available from Motic Incorporation Ltd. of Hong Kong. The high NA objective 75 is arranged to focus the illuminated image to the image capturing system 60. The high NA objective 75 also focuses fluorescence excitation light from the light source 30 onto the flow chamber 15. Further, the high NA objective 75 focuses the resulting particle fluorescence or scattered light onto the PMTs 40 of the detection system 40. The high NA objective 75 includes a lens 76 arranged to be immersed in the immersion oil 90 during imaging processes. The high NA objective 75 is selected to have a range of focus or "working distance" which ensures that focus is substantially maintained through the entirely of the cross section of the flow channel 15*a*. Further, the high NA objective 75 includes characteristics of a numerical aperture greater than 0.7 and may be the EF Plan 100×/1.25NA available from Motic Incorporation Ltd. of Hong Kong.

The immersion oil 90 is arranged to be in contact with an exterior surface of wall 16 of the flow chamber 15 and in contact with the lens 76 of the high NA objective 75 when the system 10 is in use. The immersion oil 90 has an index of refraction (n) selected to substantially match that of the wall 16 of the flow chamber 15 through which the fluid image is to be captured by the image capturing system 60. Also, the thickness of the wall 16 of the flow chamber 15 is selected to substantially match the thickness of a microscope cover slide of the type prescribed by the manufacturer of the high NA objective 75. The index of refraction (n) of the immersion oil 90 should also be selected to substantially match that of the high NA objective 75. This refractive index consistency from the high NA objective 75 through the immersion oil 90 and the wall of the flow chamber 15 to the fluid in the flow channel 15*a* keeps all of the images taken by the system 10 at their highest resolution and maximum brightness. It also optimizes the focusing of the excitation light from the light source 30 and collection of the fluorescence of passing particles. The immersion oil 90 may be the MF02020 Immersion Oil available from Motic Incorporation Ltd. of Hong Kong.

The resultant NA of the system 10 established by the arrangement of the immersion oil 90 and the oil-immersed high NA objective 75 is much higher (in a range of about 1.1 to 2.0 and generally about 1.25) than that of an air-based objective system (about 0.6). The resolution or ability to see smaller details is much smaller or finer for the system 10 as compared to prior flow cytometers in which an NA of about 0.6 is established, as evidenced by Equation (1.0):

$$\text{Resolution}=0.61*\text{wavelength of imaging}/NA \quad (1.0)$$

Optionally, the immersion oil 90 may be placed at a second location on the exterior surface of the wall 16 of the flow chamber 15 opposite from the first location on the exterior surface of the wall 16 that is adjacent to the location of the lens 76 of the high NA objective 75. This second location for the immersion oil 90 is adjacent to the location of the high NA condenser lens 95. Whereas in the arrangement previously described herein the high NA condenser lens 95 is in air when adjacent to the wall 16 of the flow chamber 15, this optional arrangement involves placement of the high NA condenser lens 95 in the immersion oil 90, in the same, but an opposing manner as is the placement of the high NA objective 75 in the immersion oil 90. The indexes of refraction of the immersion oil 90, the high NA objective 75, the high NA condenser lens 95 and the wall 16 of the flow channel 15 are preferably selected to substantially match one another. In particular, the immersion oil 90 is selected to match substantially that specified for the high NA objective 75 and the high NA condenser lens 95, including as established by the manufacturers thereof. This optional arrangement may be more difficult to build but will likely yield a resolution that is higher than the resolution available when the high NA condenser 95 is not immersed in the immersion oil 90.

The advantages associated with the high NA characteristics of the system 10 of the present invention may be readily observed by viewing the images represented in FIGS. 3-6.

Figure 3:
FIG. 3 is an image of a fluid containing yeast as captured using a prior art medium resolution optical condenser and an air objective.
Figure 4:
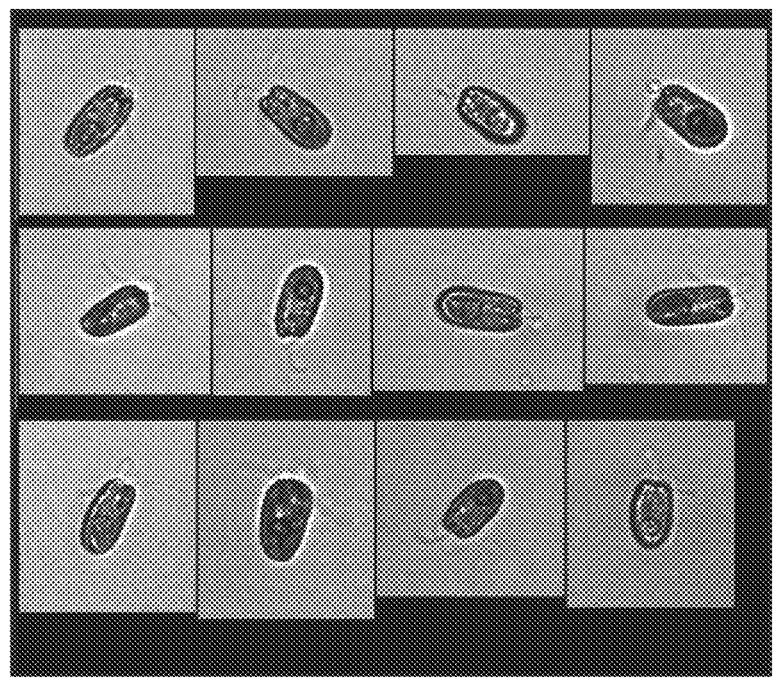
FIG. 4 is an image of the same fluid as represented in FIG. 3 but captured with the high resolution optical condenser and the oil-immersion objective of the present invention.
Figure 5:
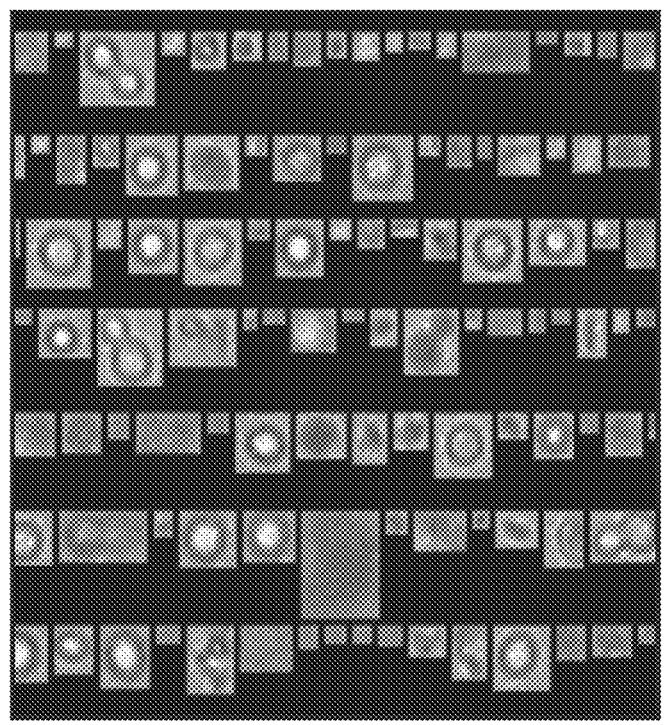
FIG. 5 is an image of a fluid containing tetraselmis as captured using a prior art medium resolution optical condenser and an air objective.
Figure 6:
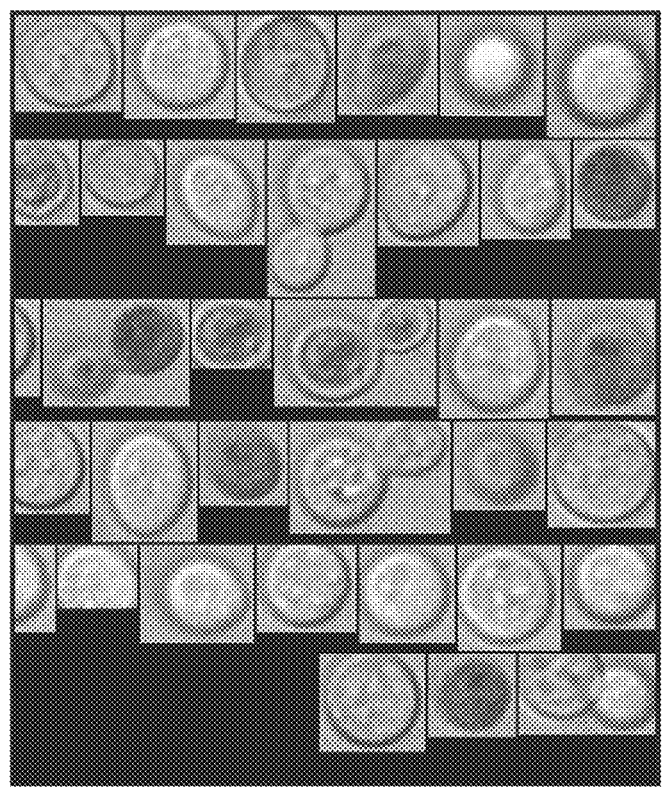
FIG. 6 is an image of the same fluid as represented in FIG. 5 but captured with the high resolution optical condenser and the oil-immersion objective of the present invention.

FIG. 3 shows a plurality of images of individual yeast cells contained in a fluid as captured using a prior flow cytometer system having a system NA of about 0.6. FIG. 4 shows a plurality of images of individual yeast cells from the same fluid but as captured using the system 10 of the present invention with a system NA of about 1.4. It can be easily observed that the system 10 of the present invention generates substantially sharper, brighter and more detailed imaging than available with the prior system. In another example of the improvement in imaging available using the system 10, FIG. 5 shows a plurality of images of individual tetraselmis cells contained in a fluid as captured using a prior flow cytometer system having a system NA of about 0.6. FIG. 6 shows a plurality of images of individual tetraselmis cells from the same fluid but as captured using the system 10 of the present invention with a system NA of about 1.4. It can be easily observed that the system 10 of the present invention generates substantially sharper, more detailed imaging than available with the prior system. In particular, individual cilia of the tetraselmis cells can be seen in the images of FIG. 6 whereas they are not observable in the images of FIG. 5.

The system 10 of the present invention with optics 35 including the high NA objective 75, the immersion oil 90 and the high NA condenser lens 95, yield flow cytometry capability that generates images that are sharper, more detailed imaging than available with existing imaging cytometry. Further, the system 10 enables the generation of images of smaller particles in a fluid, and to image smaller details of observed particles. Yet further, the system 10 enables the ability to detect smaller and/or weaker fluorescent particles.

One or more example embodiments to help illustrate the invention have been described. Nevertheless, it will be understood that various modifications may be made without departing from the spirit and scope of the invention. Accordingly, other embodiments are within the scope of the claims appended hereto.

What is claimed is:

1. A system for imaging particles in a fluid, the system comprising:
   a. a flow chamber having a refractive index, the flow chamber including a wall and a channel arranged to transport the fluid therethrough at a selectable rate; b. a light source arranged to illuminate the fluid in the flow chamber; c. a backlighting generator; d. a high numerical aperture condenser to focus backlighting from the backlight generator to the fluid in the flow chamber;
   e. an immersion oil placeable on the wall of the flow chamber in the area where the light source illuminates the fluid; f. a high numerical aperture objective including a lens placeable in the immersion oil, wherein the high numerical aperture objective is arranged to focus excitation light from the light source onto the flow chamber and to receive incident optical radiation from the flow chamber; and g. means for capturing images of particles in the fluid detected through the high numerical aperture objective.

2. The system of claim 1 wherein the wall of the flow chamber and the immersion oil have indexes of refraction that are substantially equal, and wherein the index of refraction of the immersion oil is selected to substantially match the index of refraction of the high numerical aperture objective.

3. The system of claim 1 wherein the high numerical aperture condenser and the high numerical aperture objective each have a numerical aperture in the range of about 1.1 to about 2.0.

4. The system of claim 3 wherein the high numerical aperture condenser and the high numerical aperture objective each have a numerical aperture of about 1.25.

5. The system of claim 1 wherein the generator is positioned on a side of the flow chamber opposite from the means for capturing images and arranged for generating backlighting of sufficient intensity focused by the high numerical aperture condenser lens onto the flow chamber to image particles passing therethrough.

6. The system of claim 5 wherein the backlighting generator is arranged to generate a high intensity flash at the same time that the means for capturing images is activated to capture images of particles backlit by the backlighting generator.

7. The system of claim 5 wherein the backlighting generator generates the high intensity flash when a particle has been detected passing through the flow chamber or at a selectable time interval.

8. The system of claim 1 wherein the means for capturing images includes an image capturing system and a computing device.

9. The system of claim 8 wherein the image capturing system is a video camera.

10. The system of claim 8 further comprising detection electronics.

11. The system of claim 10 wherein the detection electronics includes one or more emission filters and one or more high sensitivity photomultiplier tubes.

12. The system of claim 1 wherein the flow chamber is arranged with a rectangular shape.

13. The system of claim 1 wherein a thickness of the wall of the flow chamber substantially matches a thickness of a microscope cover slide.

14. The system of claim 1 wherein the high numerical aperture objective is selected to include a range of focus to maintain focus through a cross section of the channel of the flow chamber.

15. The system of claim 1 wherein the high numerical aperture condenser includes a lens and the immersion oil is also placed on a second location on an exterior surface of the wall of the flow chamber substantially opposite from the location of the immersion oil adjacent to the high numerical aperture objective, and wherein the lens of the high numerical condenser lens is placeable in the immersion oil at the second location.

16. The system of claim 15 wherein the wall of the flow chamber and the immersion oil have indexes of refraction that are substantially equal, and wherein the index of refraction of the immersion oil is selected to substantially match the index of refraction of the high numerical aperture objective and the high numerical aperture condenser.

* * * * *